US005747060A

United States Patent [19]
Sackler et al.

[11] Patent Number: 5,747,060
[45] Date of Patent: May 5, 1998

[54] PROLONGED LOCAL ANESTHESIA WITH COLCHICINE

[75] Inventors: Richard Sackler, Greenwich; Paul Goldenheim, Wilton, both of Conn.; Mark Chasin, Manalapan, N.J.

[73] Assignee: Euro-Celtique, S.A., Luxembourg, Luxembourg

[21] Appl. No.: 622,058

[22] Filed: Mar. 26, 1996

[51] Int. Cl.$^6$ .............................. A61K 9/14; A61K 9/52
[52] U.S. Cl. ................. 424/426; 424/195.1; 424/489; 514/818; 514/825; 514/951; 514/963
[58] Field of Search ................. 514/818, 825, 514/951, 963; 424/195.1, 489, 426

[56] References Cited

U.S. PATENT DOCUMENTS

| | | | |
|---|---|---|---|
| 3,887,699 | 6/1975 | Yolles | 424/19 |
| 4,001,388 | 1/1977 | Shell | 424/14 |
| 4,070,347 | 1/1978 | Schmitt | 260/77.5 |
| 4,164,560 | 8/1979 | Folkman et al. | 424/22 |
| 4,293,539 | 10/1981 | Ludwig et al. | 424/19 |
| 4,384,975 | 5/1983 | Fong | 427/213.36 |
| 4,419,340 | 12/1983 | Yolles | 424/19 |
| 4,569,837 | 2/1986 | Suzuki et al. | 424/28 |
| 4,623,588 | 11/1986 | Nuwayser et al. | 428/402.24 |
| 4,685,883 | 8/1987 | Jernberg | 433/215 |
| 4,725,442 | 2/1988 | Haynes | 424/490 |
| 4,757,128 | 7/1988 | Domb et al. | 528/271 |
| 4,767,628 | 8/1988 | Hutchinson | 424/426 |
| 4,780,320 | 10/1988 | Baker | 424/493 |
| 4,789,726 | 12/1988 | Hutchinson | 528/354 |
| 4,861,627 | 8/1989 | Mathiowitz et al. | 427/213.31 |
| 4,874,612 | 10/1989 | Deasy | 424/425 |
| 4,883,666 | 11/1989 | Sabel et al. | 424/422 |
| 4,888,176 | 12/1989 | Langer et al. | 424/426 |
| 4,891,225 | 1/1990 | Langer et al. | 424/428 |
| 4,906,474 | 3/1990 | Langer et al. | 424/428 |
| 4,919,939 | 4/1990 | Baker | 424/493 |
| 4,938,763 | 7/1990 | Dunn et al. | 604/891.1 |
| 5,004,602 | 4/1991 | Hutchinson | 424/78 |
| 5,019,379 | 5/1991 | Domb et al. | 424/78 |
| 5,019,400 | 5/1991 | Gombotz et al. | 424/497 |
| 5,061,492 | 10/1991 | Okada et al. | 424/423 |
| 5,122,367 | 6/1992 | Ron et al. | 424/80 |
| 5,188,837 | 2/1993 | Domb | 424/450 |
| 5,401,507 | 3/1995 | Lewis | 424/426 |

FOREIGN PATENT DOCUMENTS

| | | | |
|---|---|---|---|
| 0244118 | 11/1987 | European Pat. Off. | A61K 9/10 |
| 0430474 | 6/1991 | European Pat. Off. | A61K 9/70 |
| 9207555 | 5/1992 | WIPO | A61K 9/22 |
| 9215286 | 9/1992 | WIPO | A61K 9/22 |
| 9405265 | 3/1994 | WIPO | A61K 9/20 |

OTHER PUBLICATIONS

Wakiyama, et al, *Preparation and Evaluation in Vitro and in Vivo of Polylactic Acid Microspheres containing Dibucaine*, 1982, vol. 30, Faculty of Pharmaceutical Sciences, Hokkaido University, pp. 3719–3727.

Williams, et al., *Microencapsulated Local Anesthetics*, 1984, Biotek, Inc., pp. 69–70.

IADR Abstracts 1982, Dental Research, 1990, *Local Anesthesia and Pain III*, 3 pages.

Wall, et al., (Eds) *Textbook of Pain*, Third Edition, Publ., Churchill Livingston, pp. 94–98.

Devor, et al., 1991, *A Group Report: Mechanisms of Neuropathic Pain Following Peripheral Injury*, pp. 417–440.

Devor, et al., 1983, *Axoplasmic Transport Block Reduces Ectopic Impulse Generation in Injured Peripheral Nerves*, pp. 73–85.

Schnebel, et al., *The Use of Oral Colchicine for Low–Back Pain*, 1987, pp. 354–357.

March, et al., *Biodegradable Microspheres Containing a Colchicine Analogue Inhibit DNA Synthesis in Vascular Smooth Muscle Cells*, 1994, pp. 1929–1933.

Dunn, et al., *Monolithic Fibers For Controlled Delivery of Tetracycline*, 1980, pp. 157–159.

Lewis, et al., *The Use Of In Vitro Release Methods to Guide the Development of Controlled–Release Formulations*, Sourthern Research Institute, Alabama, pp. 61–64.

Masters, et al., *Prolonged Regional Nerve Blockade by Controlled Release of Local Anesthetic from a Biodegradable ... Matrix*, Anesthesiology, V79, No. 2, Aug. 1993, pp. 340–346.

Masters, et al., *Sustained Local Anesthetic Release from Bioerodible Polymer Matrices: A Potential Method for Prolonged ...*, 1993.

Pharmaceutical Research, vol. 10, No. 10, pp. 1527–1532.

Shah, et al., *A Biodegradable Injectable Implant for Delivering Micro and Macromolecules Using Poly(lactic-co-Glycolic) acid ...*, 1993, Journal of Controlled Release, 27, pp. 139–147, Tice, et al., *Biodegradation of Microcapsules and Biomedical Devices Prepared with Resorbable Polyesters*, 1980, Southern Research Institute and University of Alabama, pp. 21–23.

Meyers, et al., *Controlled Release of Ampicillin and Gentamicin from Biodegradable Microcapsules*, 1980, Southern Research Institute and United States Army Institute of Dental Research, pp. 108–111.

*Primary Examiner*—Michael P. Woodward
*Assistant Examiner*—Brenda Glass Brumback
*Attorney, Agent, or Firm*—Steinberg, Raskin & Davidson, P.C.

[57] ABSTRACT

A formulation for inducing sustained regional local anesthesia in a patient comprising a substrate comprising a local anesthetic and an effective amount of a biocompatible, biodegradable, controlled release material prolonging the release of the local anesthetic from the substrate to obtain a reversible nerve blockade when implanted or injected in a patient, and an amount of colchicine effective to prolong the duration of the local anesthesia for a time period longer than that obtainable from the substrate without colchicine.

33 Claims, No Drawings

PROLONGED LOCAL ANESTHESIA WITH COLCHICINE

BACKGROUND OF THE INVENTION

The present invention is related to biodegradable controlled release formulations for the administration of locally active drugs, in particular, sustained release local anesthetics in combination with colchicine for prolonging nerve block or numbness induced by a local anesthetic.

While compounds utilized as general anesthetics reduce pain by producing a loss of consciousness, local anesthetics act to induce a loss of sensation in the localized area of administration in the body. The mechanism by which local anesthetics induce their effect, while not having been determined definitively, is generally thought to be based upon the ability to interfere with the initiation and transmission of the nerve impulse. The duration of action of a local anesthetics is proportional to the time during which it is in actual contact with the nervous tissues. Consequently, procedures or formulations that maintain localization of the drug at the nerve greatly prolong anesthesia.

All local anesthetics are potentially toxic, and therefore it is of great importance that the choice of drug, concentration, rate and site of administration, as well as other actors, be considered in their use. On the other hand, a local anesthetic must remain at the site long enough to allow sufficient time for the localized pain to subside. Different devices and formulations are known in the art for administration of local anesthetics. For example, U.S. Pat. Nos. 4,725,442 and 4,622,219 (Haynes) are directed to microdroplets of methoxyflurane-containing microdroplets coated with a phospholipid prepared by sonication, which are suitable for intradermal or intravenous injection into a patient for inducing local anesthesia. Such microdroplets are said to cause long-term local anesthesia when injected intradermally, giving a duration of anesthesia considerably longer than the longest acting conventional local anesthetic (e.g., bupivacaine or dibucaine).

U.S. Pat. No. 5,188,837 (Domb) relates to a microsuspension system containing liposheres having a layer of a phospholipid imbedded on their surface. The core of the liposphere is a solid substance to be delivered, or the substance to be delivered is dispersed in an inert vehicle. The substance to be delivered can be, e.g., nonsteroidal anti-inflammatory compounds, local anesthetics, water insoluble chemotherapeutic agents and steroids.

Other formulations directed to injectable microcapsules, etc. are known. For example, U.S. Pat. No. 5,061,492 related to prolonged release microcapsules of a water-soluble drug in a biodegradable polymer matrix which is composed of a copolymer of glycolic acid and a lactic acid. The microcapsules are prepared as an injectable preparation in a pharmaceutically acceptable vehicle. The particles of water soluble drug is retained in a drug-retaining substance dispersed in a matrix of the lactic/glycolic acid copolymer in a ratio of 100/0 to 50/50 and an average molecular weight of 5,000–200,000. The injectable preparation is made by preparing a water-in-oil emulsion of aqueous layer of drug and drug retaining substance and an oil layer of the polymer, thickening and then water-drying.

U.S. Pat. No. 4,938,763 (Dunn, et al.) is related to a biodegradable polymer for use in providing syringeable, in-situ forming, solid biodegradable implants for animals. In one aspect of this reference, a thermosetting system is utilized which utilizes copolymers which may be derived from polylactides and/or polyglycolides, combinations and mixtures of these and other polymers.

U.S. Pat. No. 4,293,539 (Ludwig, et al.) is directed to controlled release formulations comprised of a microbial agent dispersed throughout a copolymer derived from lactic acid and glycolic acid. The copolymer is derived from 60–95% lactic acid and 40–5% glycolic acid by weight, and has a molecular weight of 6,000–35,000. An effective amount of the copolymeric formulation is administered by subcutaneous or intramuscular administration.

WO 94/05265 describes improved biodegradable controlled release systems consisting of a polymeric matrixs incorporating a local anesthetic for the prolonged administration of the local anesthetic agent. The devices are selected on the basis of their degradation profiles: release of the topical anesthetic in a linear, controlled manner over the period of preferably two weeks and degradation in vivo with a half-life of less than six months, more preferably two weeks, to avoid localized inflammation. The disclosure states that an anti-inflammatory can be incorporated into the polymer with the local anesthetic to reduce encapsulation for optimal access of drug to its site of action. The anti-inflammatories that are said to be useful include steroids such as dexamethasone, cortisone, prednisone, and others routinely administered orally or by injection.

Colchicine, a acetyltrimethylcolchicinic acid (N-(5,6,7,9-tetrahydro-1,2,3,10-tetramethoxy-9-oxobenzo[α]heptalen-7-yl) acetamide), is a water-soluble (about 1 gram per 22–25 ml) alkaloid of *Colchicum autumnale* that is an effective remedy for the treatment of gout. Colchicine is also widely used in research and in chromosomal studies as an antimitotic agent known for its ability to bind to microtubules and, e.g., arrest cell division. While the basis for the benefit provided by colchicine in the treatment of gout remains uncertain, it is thought to be related, in part, to the observation that colchicine suppresses leukocyte glucose metabolism, in vitro. Colchicine has also been shown to suppress injury-induced ectopic nerve discharge in a model system of chronic pain utilizing injured nerve (Wall et al. (Eds), 1995, Textbook of Pain, Third Edition, Publ., Churchill Livingston, pages 94–98; Devol et al., 1991, A Group Report: Mechanisms of neuropathic pain following peripheral injury. In: Basbaume A I, et al (eds). *TOWARDS A NEW PHARMACOTHERAPY OF PAIN*, Dahlem Konferenzen, Wiley, Chichester pp 417–440; Devor et al., 1985, Pain, 22:127–137 at 128 and Devor, 1983, Pain, 16:73–86). It has been reported in one study that colchicine was given for the treatment of low-back pain, although oral colchicine has been shown to be ineffective for the same indication (Schnebel et al., 1988, Spine 13(3):354–7).

Controlled release biodegradable microspheres of lactic acid/glycolic acid copolymer containing a colchicine analog are known (March et al., 1994, Circulation 89(5):1929–33) for the delivery of the colchicine analog to blood vessel walls to inhibit DNA synthesis in vascular smooth muscle cells.

However, colchicine is not known or used as a general analgesic, has never been reported to act as a local anesthetic and has heretofore not been known to potentiate any of the actions of local anesthetics. Further, no use of colchicine and/or analogs, derivatives and salts thereof to prolong local anesthesia is known and, in particular, no combination of a colchicine and analogs, derivatives and salts thereof, administered in combination with a sustained release form of local anesthetic, is known.

OBJECTS AND SUMMARY OF THE INVENTION

It is therefore an object of the present invention to provide a biodegradable controlled release dosage form for prolonged treatment of localized areas in humans and animals. More particularly, it is an object of the invention to provide a local anesthetic in a biocompatible, biodegradable controlled release form which provides a prolonged nerve blockade.

It is a further object of the present invention to provide a method for prolonging the effect of a local anesthetic agent at a desired site of treatment which is safe, effective, and which effectively controls post-operative pain, by administering a combination of colchicine and/or analogs, derivatives and salts thereof, or mixtures of any of the forementioned, and a local anesthetic, to a patient in need of such treatment.

It is a still further object of the present invention to prolong the duration of the nerve blockade produced by administering a local anesthetic in a sustained release form, by administering colchicine and/or analogs, derivatives and salts thereof, or mixtures of any of the forementioned, before, during or after the injection or implantation of a local anesthetic according to the invention.

In accordance with the above-mentioned objects and others, the invention is related to biodegradable and/or bioerodable controlled release formulations for the prolonged administration of a local anesthetic agent capable of providing a prolonged effect in vivo, in combination with colchicine and/or analogs, derivatives and salts thereof, or mixtures of any of the aforementioned, which is effective to prolong the duration of the local anesthetic effect for a time period greater than that possible by the use of the local anesthetic by itself and methods for the manufacture thereof are disclosed. In particular, colchicine is preferred. The local anesthetic is preferably in controlled release form. The controlled release formulation can be formed into films, slabs, pellets, microparticles, microspheres, microcapsules, spheroids, shaped devices and pastes. Preferably, the formulation is in a form suitable for suspension in isotonic saline, physiological buffer or other solution acceptable for injection into a patient.

For the convenience of the reader, the term, "colchicine" as used hereinafter also refers to analogs, derivatives and salts thereof, or mixtures of any of the forementioned.

The invention further provides methods for inducing localized anesthesia by implanting, inserting or injecting a controlled release formulation, e.g., in the form of injectable microspheres loaded with a local anesthetic in sustained release form, into a site at or adjacent to a nerve or nerves innervating a body region to provide local anesthesia. Thus, the controlled release formulation according to the invention must be injected, infiltrated or implanted at a site in a patient where the local anesthetic agent is to be released. Colchicine is optionally added to the controlled release formulation and/or included in a medium suspending the controlled release formulation, e.g., when the formulation is in the form of injectable microspheres. Colchicine can also be separately administered in a pharmaceutically acceptable composition before, during or after the controlled release formulation is administered, by any method known to the art. For example, colchicine can be administered systemically by ingestion or injection. However, it is preferred that colchicine is administered by injection at the site of the desired local nerve blockade.

Further aspects of the invention are directed to a method of treating a patient in need of a surgical procedure, comprising placing a local anesthetic in controlled release form in proximity to a nerve or nerves at the surgical site, and simultaneously and/or subsequently administering colchicine to substantially the same site to attain a prolongation of nerve blockade otherwise unattainable via the use of the local anesthetic alone. The invention also provides for a unit dosage of the controlled release formulation comprising, in a container, a sufficient amount of the formulation to induce desirable local nerve blockade in at least one patient. In one embodiment, the unit dosages are sterile and lyophilized. Alternatively, the unit dosages are sterile and prepared as suspension in a solution acceptable for injection into a patient.

The invention is further directed in part to novel formulations for providing local anesthesia, comprising a pharmaceutically-acceptable local anesthetic agent in controlled release form, said formulation being capable of being placed in proximity to a nerve which is to be anesthetized, and an effective amount of colchicine, capable of prolonging the localized numbness or nerve block provided by the local anesthetic in controlled release form. The colchicine may be incorporated with the local anesthetic, or alternatively, at east part of the dose of colchicine may be administered separately but in proximity to the same location as the local anesthetic. At least a part of such a separate dose may be administered later in time than the local anesthetic, to provide additional potentiation of the extent and/or duration of the local anesthetic effect. A portion of the local anesthetic can be administered to the desired site in immediate release form as long as a portion of the local anesthetic is also administered in controlled release form. On the other hand, the colchicine can be administered to substantially the same site at the same time as the local anesthetic, at a later time than the local anesthetic, or both, so long as the nerve blockade effect of the local anesthetic is substantially prolonged as compared to that which would be obtained with the local anesthetic alone.

In certain preferred embodiments of the invention, the local anesthetic is prepared in matrices of biodegradable controlled release injectable microspheres. In certain embodiments, the colchicine is incorporated into these matrices along with the local anesthetic.

In further embodiments, the invention is directed to a suspension comprising a plurality of biocompatible, biodegradable controlled release microspheres comprising a local anesthetic agent, which is incorporated in the controlled release microspheres, together with colchicine, which can be incorporated in the microspheres or dissolved or suspended in the microsphere suspension medium.

The suspension is, for example, suitable for administering the microspheres by injection.

In yet additional embodiments of the present invention, the local anesthetic is incorporated into a controlled release matrix to form a local anesthetic formulation or substrate having colchicine coated on the surface thereof In yet additional embodiments of the invention, the local anesthetic formulation is made up of one or more substrates which comprise a local anesthetic having colchicine present in the substrate in an amount effective to prolong the effect of the local anesthetic in an environment of use, and a biocompatible, biodegradable coating on the substrate providing a slow release of the local anesthetic and colchicine in an environment of use.

In further embodiments, a portion or all of the local anesthetic is incorporated onto an outer surface of the coated substrate.

The colchicine may be systemically administered by injection, instillation, oral dosing or other method to obtain the desired prolongation of effect. Systemic administration (e.g., oral or intravenous) will require a higher total dose of colchicine than with local administration in proximity to the local anesthetic, therefore, local injection is preferred.

The controlled release local anesthetic dosage form may be injected, with or without colchicine, at the site where the anesthetic is to be released. This can be prior to surgery, at the time of surgery, or following removal (discontinuation) or reversal of a systemic anesthetic.

In one preferred embodiment, the formulation is prepared in the form of microspheres. The microsphere may be a homogenous matrix of a local anesthetic with a biodegradable controlled release material, optionally with colchicine incorporated therein. The microspheres are preferably prepared in sizes suitable for injection, and injected at the site where the anesthetic is to be released before surgery, during the time of surgery, or following removal or reversal of systemic anesthetic.

Examples demonstrate prolongation of the duration of local anesthesia with the greater prolongation being provided by the combination of a local anesthetic with colchicine.

DETAILED DESCRIPTION

Formulations and methods for the controlled and prolonged delivery of a local anesthetic agent to a targeted area are provided. These systems can be used for the management of various forms of persistent pain, such as postoperative pain, sympathetically maintained pain, or certain forms of chronic pain such as the pain associated with many types of cancer. These systems may also be used for blockade of nociceptive pathways (afferent and efferent) in patients with acute pancreatitis, ileus, or other visceral disorders.

As used herein, the term "local anesthetic agent" means any drug which provides local numbness and/or analgesia. Simply by way of example and without limitation, local anesthetic agents which can be used include bupivacaine, ropivacaine, dibucaine, procaine, chloroprocaine, prilocaine, mepivacaine, etidocaine, tetracaine, lidocaine, and xylocaine, and mixtures thereof. The local anesthetic can be in the form of a salt, for example, the hydrochloride, bromide, acetate, citrate, carbonate or sulfate. More preferably, the local anesthetic agent is in the form of a free base. The free base provides a slower initial release and avoids an early "dumping" of the local anesthetic at the injection site. Preferred local anesthetic agents include, e.g., bupivacaine. Bupivacaine is a particularly long acting and potent local anesthetic agent when incorporated into a pellet or other controlled release formulation. Its other advantages include sufficient sensory anesthesia without significant motor blockade, lower toxicity, and wide availability. Anesthetic typically administered systematically may also be used in those cases where the means of administration results only in a local effect, rather than systemic. The term "local anesthetic" may also encompass, pursuant to the definitions provided herein, a drug of a different class than those traditionally associated with local anesthetic properties, including but not limited to morphine, fentanyl, and agents which, for example, can provide regional blockade of nociceptive pathways (afferent and/or efferent).

As used herein, the term "patient" broadly refers to any animal that is to be treated with the compositions and by the methods herein disclosed. The disclosed local anesthetic dosage form can provide localized pain blockade to any animal (including humans), e.g., any vertebrate, which it is desired to so anesthetize. In one embodiment, the disclosed methods and compositions will find use in veterinary practice and animal husbandry for, e.g., birds and mammals, wherever prolonged local anesthesia is convenient or desirable. In a preferred embodiment, the term includes humans in need of or desiring prolonged local anesthesia.

In another preferred embodiment, colchicine prolongs the duration of the local anesthetic effect produced by the release of local anesthetic at a site in a patient from a sustained release composition, relative to the duration of the local anesthetic effect without colchicine, without substantially changing the rate of release of the local anesthetic agent from the sustained release composition.

In a further aspect, colchicine increases the magnitude or degree of the local anesthesia effect (e.g., as measured by a higher latency in a foot withdrawal test in a test animal) while increasing the duration of the local anesthetic action.

Although colchicine is known as an microtubule inhibitor and antimitotic agent, the mechanism for the prolongation of the action of a local anesthetic is not presently known. Thus, while colchicine is preferred, the artisan will understand that it is possible that other compounds might work in a related fashion. Such related compounds, including colchicine analogs, derivatives, salts and mixtures thereof, as well as other compounds known to the art, are considered to be part of the present invention.

Any formulation suitable for local implantation or injection in proximity to a nerve that is able to provide a controlled release of a local anesthetic agent may be employed to provide for prolonged local anesthesia as needed. Slow release formulations known in the art include specially coated pellets, polymer formulations or matrices for surgical insertion or as controlled release microparticles or microspheres for implantation, insertion or injection, wherein the slow release of the active medicament is brought about through controlled diffusion out of the matrix and/or selective breakdown of the coating of the preparation or selective breakdown of a polymer matrix.

It has surprisingly been discovered that the use of colchicine in conjunction with a controlled release local anesthetic agent significantly increases the time period of nerve blockade. The increase in efficacy provided by the use of colchicine cannot be predicted based on in vitro release (dissolution) of the local anesthetic in controlled release form. In other words, the inclusion of colchicine within the controlled release formulations of the invention does not substantially alter or prolong the in vitro dissolution rate of the local anesthetic agent from the formulation; yet, the same formulation when administered in vivo provides a significant increase in the time period of nerve blockade at the site of administration. It is further been discovered that such colchicine can be administered prior to, along with, or after injection of the local anesthetic agent in controlled release form, in each case with a substantial prolongation of nerve blockade in vivo.

Colchicine can be compounded in the same controlled release formulation as a local anesthetic agent, in a separate controlled release formulation, e.g., different injectable microspheres, or in a non-controlled release formulation such as, for example, the diluent or carrier solution, or suspension of the injectable microspheres. The colchicine may be administered before, simultaneously with, or after injection, implantation or insertion of the controlled release local anesthetic formulation at the desired site by any art-known method.

In those embodiments of the invention directed to formulations where colchicine is included, the colchicine may be included in controlled release form or in immediate release form. The colchicine may be incorporated into, e.g., the controlled release matrix along with the local anesthetic; incorporated into a controlled release coating on a controlled release device or formulation; or incorporated as an immediate release layer coating the local anesthetic formulation. On the other hand, the colchicine may be incorporated into a pharmaceutically acceptable aqueous medium suitable for injection, either in controlled release form or in immediate release form. The preferred embodiment contains the colchicine in a controlled-release device or formulations.

The controlled release formulations and methods of the invention may be used in conjunction with any implantable, insertable or injectable system known in the art, including but not limited to microspheres, microcapsules, gels, pastes, implantable rods, pellets, plates or fibers, and the like (generically referred to as "substrates").

In a preferred embodiment, the slow release formulation is prepared as microspheres in a size distribution range suitable for local injection. The diameter and shape of the microspheres or other particles can be manipulated to modify the release characteristics. For example, larger diameter microspheres will typically provide slower rates of release and reduced tissue penetration and smaller diameters of microspheres will produce the opposite effects, relative to microspheres of different mean diameter but of the same composition. In addition, other particle shapes, such as, for example, cylindrical shapes, can also modify release rates by virtue of the increased ratio of surface area to mass inherent to such alternative geometrical shapes, relative to a spherical shape. The diameter of injectable microspheres are in a size range from, for example, from about 5 microns to about 200 microns in diameter. In a more preferred embodiment, the microspheres range in diameter from about 20 to about 120 microns.

A wide variety of biodegradable materials may be utilized to provide the controlled release of the local anesthetic. Any pharmaceutically acceptable biodegradable polymers known to those skilled in the art may be utilized. It is preferred that the biodegradable controlled release material degrade in vivo over a period of less than about two years, with at least 50% of the controlled release material degrading within about one year, and more preferably six months or less. More preferably, the controlled release material will degrade significantly within one to three months, with at least 50% of the material degrading into non-toxic residues which are removed by the body, and 100% of the drug being released within a time period from about two weeks to about two months. The controlled release material should preferably degrade by hydrolysis, and most preferably by surface erosion, rather than by bulk erosion, so that release is not only sustained but also provides desirable release rates. However, the pharmacokinetic release profile of these formulations may be first order, zero order, bi- or multi-phasic, to provide the desired reversible local anesthetic effect over the desired time period.

The controlled release material should be biocompatible. In the case of polymeric materials, biocompatibility is enhanced by recrystallization of either the monomers forming the polymer and/or the polymer using standard techniques.

Suitable biodegradable polymers can be utilized as the controlled release material. The polymeric material may comprise a polylactide, a polyglycolide, a poly(lactide-co-glycolide), a polyanhydride, a polyorthoester, polycaprolactones, polyphosphazenes, polysaccharides, proteinaceous polymers, soluble derivatives of polysaccharides, soluble derivatives of proteinaceous polymers, polypeptides, polyesters, and polyorthoesters. The polysaccharides may be poly-1,4-glucans, e.g., starch glycogen, amylose, amylopectin, and mixtures thereof. The biodegradable hydrophilic or hydrophobic polymer may be a water-soluble derivative of a poly-1,4-glucan, including hydrolyzed amylopectin, hydroxyalkyl derivatives of hydrolyzed amylopectin such as hydroxyethyl starch (HES), hydroxyethyl amylose, dialdehyde starch, and the like. Preferred controlled release materials which are useful in the formulations of the invention include the polyanhydrides, co-polymers of lactic acid and glycolic acid wherein the weight ratio of lactic acid to glycolic acid is no more than 4:1 (i.e., 80% or less lactic acid to 20% or more glycolic acid by weight), and polyorthoesters containing a catalyst or degradation enhancing compound, for example, containing at least 1% by weight anhydride catalyst such as maleic anhydride. Other useful polymers include protein polymers such as gelatin and fibrin and polysaccharides such as hyaluronic acid. Since polylactic acid takes at least one year to degrade in vivo, this polymer should be utilized by itself only in circumstances where such a degradation rate is desirable or acceptable.

Proteinaceous polymers may also be used. Proteinaceous polymers and their soluble derivatives include gelation biodegradable synthetic polypeptides, zein, elastin, alkylated collagen, alkylated elastin, and the like. Biodegradable synthetic polypeptides include poly-(N-hydroxyalkyl)-L-asparagine, poly-(N-hydroxyalkyl)-L-glutamine, copolymers of N-hydroxyalkyl-L-asparagine and N-hydroxyalkyl-L-glutamine with other amino acids. Suggested amino acids include L-alamine, L-lysine, L-phenylalanine, L-valine, L-tyrosine, and the like.

In embodiments where the biodegradable polymer comprises a gel, one such useful polymer is a thermally gelling polymer, e.g., polyethylene oxide, polypropylene oxide (PEO-PPO) block copolymer such as Pluronic® F127 from BASF Wyandotte. In such cases, the local anesthetic formulation may be injected via syringe as a free-flowing liquid, which gels rapidly above 30° C. (e.g., when injected into a patient). The gel system then releases a steady dose of local anesthetic at the site of administration.

In additional embodiments of the invention, the controlled release material, which in effect acts as a carrier for the local anesthetic, can further include a bioadhesive polymer such as pectins (polygalacturonic acid), mucopolysaccharides (hyaluronic acid, mucin) or non-toxic lectins or the polymer itself may be bioadhesive, e.g., polyanhydride or polysaccharides such as chitosan.

Definitions or further descriptions of any of the foregoing terminology are well known in the art and may be found by referring to any standard biochemistry reference text such as "Biochemistry" by Albert L. Lehninger, Worth Publishers, Inc. and "Biochemistry" by Lubert Stryer, W.H. Freeman and Company, both of which are hereby incorporated by reference.

The aforementioned biodegradable polymers are particularly suited for the methods and compositions of the present invention by reason of their characteristically low human toxicity and virtually complete biodegradability.

The substrates of the presently described formulations are preferably manufactured using a method that evenly disperses the local anesthetic throughout the formulation, such as emulsion preparation, solvent casting, spray drying or hot melt, rather than a method such as compression molding. A desired release profile can be achieved by using a mixture of polymers having different release rates and/or different percent loading of local anesthetic and/or colchicine, for example, polymers releasing in one day, three days, and one week, so that linear release is achieved even when each polymer per se does not release linearly over the same time period. In addition, a mixture of microspheres having one or more different local anesthetic agents, having the same or different controlled release profile, can be utilized to provide the benefits of different potencies and spectrum of activity during the course of treatment.

Methods for manufacture of microspheres are well known and are typified in the following examples. Examples of suitable methods of making microspheres include solvent evaporation, phase separation and fluidized bed coating.

In solvent evaporation procedures, the local anesthetic agent, if soluble in organic solvents, may be entrapped in the biodegradable polymer by dissolving the polymer in a volatile organic solvent, adding the drug to the organic phase, emulsifying the organic phase in water which contains less than 2% polyvinyl alcohol, and finally removing the solvent under vacuum to form discrete, hardened monolithic microspheres.

Phase separation microencapsulation procedures are suitable for entrapping water-soluble agents in the polymer to prepare microcapsules and microspheres. Phase separation involves coacervation of the polymer from an organic solvent by addition of a nonsolvent such as silicone oil.

In fluidized bed coating, the drug is dissolved in an organic solvent along with the polymer. The solution is then processed, e.g., through a Wurster air suspension coater apparatus to form the final microcapsule product.

The biodegradable controlled release materials may be used in order to prepare controlled release local anesthetic implants. The implants may be manufactured, e.g., by compression molding, injection molding, and screw extrusion, whereby the local anesthetic agent is loaded into the polymer. Implantable fibers can be manufactured, e.g., by blending the local anesthetic agent with the controlled release material and then extruding the mixture, e.g., under pressure, to thereby obtain biodegradable fibers. In certain preferred embodiments, the colchicine may be incorporated into the implant, or may be coated onto a surface of the implant.

In other embodiments of the invention, the controlled release material comprises an artificial lipid vesicle, or liposome. Liposomes are well known in the art as carriers of bioactive or pharmacologically active substances such as drugs. Liposomes as described herein will vary in size. Preferably, the liposomes have a diameter between 100 nm and 10 microns or greater. A wide variety of lipid materials may be used to form the liposomes including natural lecithins, e.g., those derived from egg and soya bean, and synthetic lecithins, the proviso being that it is preferred that the lipids are non-immunogenic and bio-degradable. Also, lipid-based materials formed in combination with polymers may be used, such as those described in U.S. Pat. No. 5,188,837 to Domb, (incorporated by reference herein).

Examples of synthetic lecithins which may be used together with their respective phase transition temperatures, are di-(tetradecanoy)phosphatidylcholine (DTPC) (23° C.), di-(hexadecanoyl)phosphatidylcholine (DHPC) (41° C.) and di-(octandecanoyl) phosphatidylcholine (DOPC) (55° C). Di-(hexadecanoyl) phosphatidycholine is preferred as the sole or major lecithin, optionally together with a minor proportion of the di-(octadecanoyl) or the di-(tetradecanoyl) compound. Other synthetic lecithins which may be used are unsaturated synthetic lecithins, for example, di-(oleyl) phosphatidyl-choline and di-(linoleyl)phosphatidylcholine. In addition to the main liposome-forming lipid or lipids, which are usually phospholipids, other lipids (e.g. in a proportion of 5 . 40% w/w of the total lipids) may be included, for example, cholesterol or cholesterol stearate, to modify the structure of the liposome membrane, rendering it more fluid or more rigid depending on the nature of the main liposome-forming lipid or lipids.

In certain embodiments, the colchicine is incorporated along with the local anesthetic agent into the lipid. In other preferred formulations, the lipids containing the local anesthetic agent are dispersed in a pharmaceutically acceptable aqueous medium. The colchicine may also be incorporated into this aqueous medium. In a further embodiment, a portion of the dose of the local anesthetic is incorporated into the aqueous medium in immediate release form. The resultant formulation is an aqueous suspension which may comprise the local anesthetic and/or colchicine partitioned between a free aqueous phase and a liposome phase.

As an even further alternate embodiment, liposomes containing local anesthetic may be combined in an aqueous phase with liposomes containing the colchicine to form an aqueous pharmaceutical suspension useful for administration at the desired site in the patient to be anesthetized. This may be accomplished via injection or implantation. Liposomes may be prepared by dissolving an appropriate amount of a phospholipid or mixture or phospholipids together with any other desired lipid soluble components (e.g., cholesterol, cholesterol stearate) flowing in a suitable solvent (e.g., ethanol) and evaporating to dryness. An aqueous solution of the local anesthetic, optionally with colchicine, may then be added and mixed until a lipid film is dispersed. The resulting suspension will contain liposomes ranging in size, which may then fractionated to remove undesirable sizes, if necessary. This fractionation may be effected by column gel chromatography, centrifugation, ultracentrifugation or by dialysis, as well known in the art.

The above method of preparation of liposomes is representative of a possible procedure only. Those skilled in the art will appreciate that there are many different methods of preparing liposomes, all of which are deemed to be encompassed by the present disclosure.

In certain embodiments where the substrate is a microsphere, the microspheres include from about 5% to about 95% drug and from about 5% to about 95% polymer, by weight. In certain preferred embodiments, the drug is included in the microspheres in an amount from about 20% to about 90%, more preferably from about 60% to about 80%, and most preferably from about 65 to about 75% (high-load microspheres).

The term "microspheres" are defined for purposes of the present invention as particles comprising local anesthetic and the aforementioned polymeric materials (used as a controlled release carrier for the drug) which are preferably anywhere from about 20 microns to about 200 microns, and more preferably from about 45 to about 90 microns in diameter. The microspheres are preferably formed in such a size as to be injectable. For purposes of the present invention, the term "microsphere" encompasses "microparticle" and "microcapsule". The polymeric material used in the microspheres of the present invention preferably have a molecular weight from about 5,000 to about 200,000.

The polymeric material may be prepared by any method known to those skilled in the art. For example, where the polymeric material is comprised of a copolymer of lactic and glycolic acid, this copolymer may be prepared by the procedure set forth in U.S. Pat. No. 4,293,539 Ludwig, et al.), hereby incorporated by reference. Basically, therein the copolymers are prepared by condensation of lactic acid and glycolic acid in the presence of a readily removable polymerization catalyst (e.g., a strong acid ion-exchange resin such as Dowex HCR-W2-H). The amount of catalyst is not critical to the polymerization, but typically is form about 0.01 to about 20 parts by weight relative to the total weight of combined lactic acid and glycolic acid. The polymerization reaction may be conducted without solvents at a temperature from about 100° C. to about 250° C. for about 48 to about 96 hours, preferably under a reduced pressure to facilitate removal of water and by-products. The copolymer is then recovered by filtering the molten reaction mixture to remove substantially all of the catalyst, or by cooling and then dissolving the reaction mixture in an organic solvent such as dichloromethane or acetone and then filtering to remove the catalyst.

Polyanhydrides may be prepared in accordance with the methods set forth in U.S. Pat. No. 4,757,128, hereby incorporated by reference. For example, polyanhydrides may be synthesized by melt polycondensation of highly pure dicarboxylic acid monomers converted to the mixed anhydride by reflux in acetic anhydride, isolation and purification of the isolated prepolymers by recrystallization, and melt polymerization under low pressure ($10^{-4}$ mm) with a dry ice/acetone trap at a temperature between 140°–250° C. for 10–300 minutes. High molecular weight polyanhydrides are obtained by inclusion of a catalyst which increases the rate of anhydride interchain exchange, for example, alkaline earth metal oxides such as CaO, BaO and $CaCO_3$. Polyorthoester polymers may be prepared, e.g., as set forth in U.S. Pat. No. 4,070,347, hereby incorporated by reference.

Various commercially available poly (lactide-co-glycolide) materials (PLGA) may be used in the preparation of the microspheres of the present invention. For example, poly(d,l-lactic-co-glycolic acid) are commercially available from Medisorb Technologies International L.P. (Cincinnati, Ohio). A preferred product commercially available from Medisorb is a 50:50 poly (D,L) lactic co-glycolic acid known as MEDISORB 5050 DL. This product has a mole percent composition of 50% lactide and 50% glycolide. Other suitable commercially available products are Medisorb 65:35 DL, 75:25 DL, 85:15 DL and poly(d,l-lactic acid) (d,l-PLA). Poly(lactide-co-glycolides) are also commercially available from Boerhinger Ingelheim (Germany) under its Resomer© mark, e.g., PLGA 50:50 (Resomer RG 502), PLGA 75:25 (Resomer RG 752) and d,l-PLA (resomer RG 206), and from Birmingham Polymers (Birmingham, Ala.). These copolymers are available in a wide range of molecular weights and ratios of lactic to glycolic acid.

The polymers utilized in the microspheres of the present invention may be prepared, e.g., by the condensation of lactic acid and glycolic acid in the presence of a readily removable polymerization catalyst. Such catalysts include strong acid ion-exchange resins in the form of beads or similarly hard structures which are easily removed by filtration or similar techniques. Further information concerning the preparation of the copolymers of the present invention is readily available to those skilled in the art, and may be ascertained from, e.g., U.S. Pat. No. 4,293,539 (Ludwig, et al.), hereby incorporated by reference.

Pharmaceutically acceptable polyanhydrides which are useful in the present invention have a water-labile anhydride linkage. The rate of drug release can be controlled by the particular polyanhydride polymer utilized and its molecular weight. The polyanhydride polymer may be branched or linear. Examples of polyanhydrides which are useful in the present invention include homopolymers and copolymers of poly(lactic acid) and/or poly(glycolic acid), poly[bis(p-carboxyphenoxy)propane anhydride] (PCPP), poly[bis(p-carboxy)methane anhydride] (PCPM), polyanhydrides of oligomerized unsaturated aliphatic acids, polyanhydride polymers prepared from amino acids which are modified to include an additional carboxylic acid, aromatic polyanhydride compositions, and co-polymers of polyanhydrides with other substances, such as fatty acid terminated polyanhydrides, e.g., polyanhydrides polymerized from monomers of dimers and/or trimers of unsaturated fatty acids or unsaturated aliphatic acids.

The biodegradable controlled release microspheres of the present invention may be prepared by any procedure known to those skilled in the art. In certain preferred embodiments, however, the microspheres may be obtained by utilizing a solvent extraction technique (reactor process) which involves dissolving the drug and the polymer in an organic solvent such as ethyl acetate. This solution thereby obtained (the dispersed phase) is added to a solution of, e.g., polyvinyl alcohol (PVA) in water (the continuous phase) with stirring. The emulsion thereby formed is then added to water in order to extract the solvent and to harden the microspheres. The mixture is then filtered and the microspheres are dried. One appropriate method of drying is, e.g., under vacuum at room temperature. The desired particle size fraction is then collected by sieving. The organic solvent utilized is preferably ethyl acetate; however, any pharmaceutically acceptable organic solvent may be utilized, such as acetone, ethanol, diethyl ether, methanol, benzyl alcohol, methylene chloride, petroleum ether or others. This procedure is particularly useful for preparing microspheres of bupivacaine base.

Alternatively, the microspheres of bupivacaine base may be prepared by dissolving the drug and polymer in ethyl acetate and thereafter spray drying the solution.

In instances where the microspheres are to incorporate drugs which are very water soluble and insoluble in ethyl acetate, such as bupivacaine HCl, the microspheres may be prepared using a coacervation/phase separation rather than the solvent extraction technique described above. However, the solvent extraction technique can be used with bupivacaine HCl due to its low water solubility at pH 7.4 and above. The coacervation/phase separation technique utilized involves dissolving the polymer in ethyl acetate and suspending micronized bupivacaine HCl in the solution. Silicone oil is then added to form the microspheres. This mixture is then added to heptane to harden the microspheres, which are then separated by filtration. The microspheres are dried under a vacuum at room temperature. The desired particle size fraction is then collected by sieving.

Alternatively, microspheres prepared using bupivacaine HCl may be accomplished by suspending the drug in a solution of polymer in ethyl acetate or in methylene chloride and methanol and spray drying.

Alternatively, the bupivacaine HCl may be dissolved in water, and the polymer may be dissolved in ethyl acetate. The water phase then can be added to the organic phase and homogenized to yield a W/O emulsion. The drug being in the water phase would then be surrounded by polymer (oil phase). This is then added to the PVA solution in water with stirring to form a W/O/W emulsion. The solvent would diffuse out, leaving microspheres. Additional cold water can be added to harden the microspheres. This process may yield more uniform microspheres without requiring micronization of the drug. Also, as the drug will be surrounded by polymer, the release of the drug may be more uniform and would be diffusion-controlled.

The ultimate drug content of the microspheres according to the present invention may be varied substantially, depending upon whether a high load or a low load formulation procedure is utilized. In certain preferred embodiments (e.g., where the drug is bupivacaine), the drug content of the high-load microspheres may be from about 40% to about 95% of the total weight of the microsphere, and the drug content of the low-load microspheres may be from about 5% to about 40%.

In one preferred embodiment of the present invention, the drug included in the microspheres is a local anesthetic either of the ester or amide type. Suitable local anesthetics of the ester type include the benzoic acid esters (e.g., piperocaine, meprylcaine, isobucaine), the para-aminobenzoic acid esters (e.g., procaine, tetracaine, butethamine, propoxycaine, chloroprocaine); meta-aminobenzoic acid esters (e.g., metabutethamine, primacaine), paraethoxybenzoic acid esters (e.g., parethoxycaine), and their pharmaceutically acceptable salts. The non-esters include, e.g., lidocaine, mepivacaine, pyrrocaine, prilocaine, bupivacaine, etidocaine, pharmaceutically acceptable salts. A most preferred local anesthetic is bupivacaine.

In certain preferred embodiments of the present invention, the microspheres incorporate bupivacaine as the drug in an amount from about 45% to about 70% by weight, the copolymer being PLGA 50:50 of a molecular weight from about 5,000 to about 200,000.

The microspheres of the present invention preferably provide a sustained action in the localized area to be treated. For example, when the drug included in the microspheres is bupivacaine, it would be desirable that such a formulation could provide localized anesthesia to the area in question for a period of one day, two days, three days, or longer. The formulations can therefore, of course, be modified in order to obtain such a desired result.

The microspheres of the present invention may be utilized as a controlled release formulation preferably by incorporating an effective amount of the same into a pharmaceutically acceptable medium, e.g., aqueous solution or suspension, for injection. The final reconstituted product viscosity is understood to be in a range suitable for the route of administration. In certain instances, the final reconstituted product viscosity may be, e.g., about 35 cps. Administration may be via the subcutaneous or intramuscular route. However, alternative routes are also contemplated, and the formulations may be applied to the localized site in any manner known to those skilled in the art, such that a localized effect is obtained. The microspheric formulations of the present invention can be implanted at the site to be treated. Thereby, the formulations of the present invention, when including a local anesthetic, may be used in the control of post-operative pain.

The dosage of the controlled release microsphere formulations of the present invention is dependent upon the kind and amount of the drug to be administered, the recipient animal, and the objectives of the treatment. For example, when the drug included in the microspheres of the present invention is bupivacaine, the formulation may include, e.g., from about 0.5 to about 2 mg/kg body weight. The effective dose of bupivacaine, or an amount of another local anesthetic sufficient to provide proportional potency, can range from about 1 to 50 mg of bupivacaine injected or inserted at each site where the release of a local anesthetic agent is desired. In certain preferred embodiments, the dose of bupivacaine in the controlled release dosage form of the invention is sufficient to provide a controlled release of about 1 to 4 mg per day at the release site for at least 1 to 4 days. Since the formulations of the present invention are controlled release, it is contemplated that formulations may include much more than usual immediate release doses, e.g., as much as 120 mg/kg bupivacaine or more.

The local anesthetic is incorporated into the polymer or other controlled-release formulation in a percent loading between 0.1% and 90% by weight, preferably between 5% and 75% by weight. It is possible to tailor a system to deliver a specified loading and subsequent maintenance dose by manipulating the percent drug incorporated in the polymer and the shape of the matrix or formulation, in addition to the form of local anesthetic (e.g., free base versus salt) and the method of production. The amount of drug released per day increases proportionately with the percentage of drug incorporated into the formulation, e.g., matrix (for example, from 5 to 10 to 20%). In the preferred embodiment, polymer matrices or other formulations with about 75% drug incorporated are utilized, although it is possible to incorporate substantially more drug, depending on the drug, the method used for making and loading the device, and the polymer.

The formulation of controlled release substrate comprising local anesthetic provides from about 10 to about 60 percent release of local anesthetic after 24 hours, from about 20 to about 80 percent release after 48 hours and from about 40 to about 100 percent release after 72 hours.

In a preferred embodiment, the formulation of controlled release substrate comprising local anesthetic provides from about 25 to about 40 percent release of local anesthetic after 24 hours, from about 40 to about 50 percent release after 24 hours and from about 45 to about 55 percent release after 72 hours and 80 to 100 percent cumulative release is provided after about 280 hours.

In order to obtain a local anesthetic effect in vivo when combined with the colchicine as described herein of at least about 180 hours, the colchicine is placed into approximately the same site in a patient (e.g., human or veterinary) before, simultaneously with, or after the placement of a local anesthetic at that site. Alternatively, the colchicine can be administered systemically before, during or after administration of a local anesthetic into the patient.

In a preferred embodiment the local anesthetic effect is prolonged by the use of an colchicine from 2 to 15 times the duration of the local anesthetic effect that is obtained from the same formulation without benefit of colchicine. The duration of the local anesthetic effect prolonged by colchicine ranges from about 24 to about 200 hours or greater. Further, the duration of the local anesthetic effect prolonged by a colchicine can range from about 24 to about 180 hours or greater, or from about 48 to about 120 hours or greater.

The rate of release of local anesthetic agent or other drugs incorporated into the formulation will also depend on the solubility properties of the local anesthetic or drug. The greater the solubility in water, the more rapid the rate of release in tissue, all other parameters being unchanged. For example, those local anesthetic agents having pH dependent solubility will be released more rapidly at the optimum pH for those compounds. Thus, the formulation may be optimized for the desired local anesthetic release rate by selecting local anesthetic agents having a desired water solubility in tissue, e.g., at tissue pH. Thus, a local anesthetic agent that is more soluble at acid pH will have a faster release rate in a relatively acidic (e.g., pH less than about 7.2) tissue. For example, in one embodiment, the formulation will have released, in vitro, at least 70 percent of a local anesthetic at 48 hours at about pH 6 and will have released at least 40 percent of a local anesthetic at a pH ranging from about 7.4 to about 8, at 48 hours. Other combinations are pH independent in their release.

When the colchicine is included in the vehicle or carrier solution suspending controlled release substrates (e.g., microspheres) comprising local anesthetic, it has been found that useful loadings of colchicine are from 0.01% to 10%, or from about 0.01% to about 5% by weight of the local anesthetic, or from about 0.5% to about 1% of the dosage form. In one aspect the colchicine is present, relative to the weight of local anesthetic from about 0.01% to about 10% relative to the weight of the local anesthetic or from about 0.5% to about 1. The dosage must be low enough to avoid toxicity when the colchicine is included in a controlled release substrate together with or separated from one or more local anesthetic agents. When the colchicine is included in a controlled release substrate together with, or separately from one or more local anesthetic agents, the weight ratios of local anesthetic to colchicine are the same as discussed above for solution-based agents. Of course, these ratios are calculated with respect to colchicine and bupivacaine and the artisan will appreciate that these ratios can be adjusted relative to the potency of other local anesthetic agents and colchicine, as might be conveniently employed, relative to bupivacaine and colchicine, respectively.

The examples demonstrate that colchicine prolongs the duration of nerve blockade in vivo.

Potential applications include any condition for which localized nerve blockade is desirable. This includes both nerve blockade for the relief of pain and motor symptoms as well as nerve blockade for other medical purposes. The formulations and methods according to the invention can be used to provide from 1 to 7 days or more of effective intercostal blockade for thoracotomy, or longer term intercostal blockade for thoracic post-therapeutic neuralgia, lumbar sympathetic blockade for reflex sympathetic dystrophy, or three-day ilioinguinal/iliohypogastric blockade for hernia repair. Other potential applications include obstetrical or gynecological procedures. Yet further potential applications include providing localized temporary sympathectomy, e.g., blockade of sympathetic or parasympathetic ganglia to treat a variety of autonomic diseases, including circulatory dysfunction or cardiac dysrhythmias. The formulations may also be used to treat trigeminal neuralgia and other diseases of the cranial nerves as well as to provide temporary nerve blockade to treat localized muscle spasm and treatment of retrobulbar conditions, e.g., eye pain. Other uses include intra-operative administration in order to reduce pain during and after the operative procedure, especially for plastic surgery procedures where prolonged nerve blockade will enhance the outcome. These are merely examples, and additional uses for both human and veterinary practice are immediately apparent to the artisan.

Methods of Administration

In a preferred method of administration a dosage form, e.g., microspheres, are administered by injection into a site where local anesthetic agent is to be released. Microspheres may be injected through a syringe or a trochar. Pellets or slabs may be surgically placed into a site where release of oral anesthetic agent is desired.

As described below, microspheres according to the invention can be administered alone or in combination with a solution including colchicine in an amount effective to prolong the duration of local nerve blockade. Alternatively, the microspheres include, in addition to a local anesthetic, an amount of colchicine effective to prolong the duration of local nerve blockade. In another aspect, the colchicine alone is present in a controlled release microsphere and the local anesthetic is provided in solution and/or suspension.

In another alternative, colchicine can be administered before, simultaneously with or after administration of the controlled release local anesthetic, wherein the colchicine is formulated into a separate microsphere formulation for controlled release. The controlled release rate for the colchicine may be the same as or different than the controlled release rate for the local anesthetic. In a further embodiment, an additional dose of colchicine may also be administered as an injectable solution, in an injectable carrier or in a controlled release carrier to the nerve to be blockaded after the controlled release local nerve blockade has worn off, in order to reactivate the initial nerve blockade without the co-administration of additional local anesthetic.

The microspheres may be prepared from PLGA polymers ranging from, for example, PLGA in a ratio of 50/50, 65/35 or 75/25. An optimum composition has been determined to be PLGA 65/35. The microspheres, formulated with, e.g., PLGA 65/35, are administered in a dose ranging from, for example, 2 through 450 mg of microspheres 75% (w/w) loaded with a local anesthetic such as bupivacaine, per kg of the patient to be treated. In a preferred embodiment the dose ranges from 50 through 450 mg/kg. In a more preferred embodiment the dose ranges from about 10 to about 150 mg/kg with PLGA 65/35. Certainly, the artisan will appreciate the fact that the dose ranges mentioned above are based on the potency of bupivacaine, and that exact effective dosages will vary with the particular relative potency and pharmacokinetics of each local anesthetic and will be able to readily adjust the dose according to the degree of blockade experienced by the patient.

The use of colchicine before, simultaneously with or after administration of a controlled release local anesthetic, results in prolonged anesthesia.

The formulation described herein can also be used to administer local anesthetic agents that produce modality-specific blockade, as reported by Schneider, et al., Anesthesiology, 74:270–281 (1991), or that possess physical-chemical attributes that make them more useful for sustained release then for single injection blockade, as reported by Masters, et al., Soc. Neurosci. Abstr., 18:200 (1992), the teachings of which are incorporated herein.

DETAILED DESCRIPTION OF THE PREFERRED EMBODIMENTS

The following non-limiting examples illustrate the preparation of the formulations according to the invention and the effects of local anesthetic and colchicine alone and in combination.

EXAMPLE 1

Effect of Colchicine on Duration of Latency

I. Hot-Plate Test Methodology

Sprague Dawley rates with an average weight of 275 gm were brought to a test room and allowed 24 hours to recover from transport an dandling. The hot-plate test consisted of gently holding the body of the animal while the plantar aspect of the paw was placed on the hot-plate. The baseline (control) latency for the rat to withdraw its paw from the hot-plate (56° C.) was determined prior to unilateral infiltration of long-acting bupivacaine microspheres (150 mg/kg) around the sciatic nerve. Diluent containing colchicine was added to the microspheres 6 min. before injection. Rats were briefly anesthetized with ether during the injection protocol to prevent voluntary skeletal muscle contraction during the nerve stimulation procedure. A 22 gauge 4 STIMEX parylene coated needle was placed in the lumen of an 18 gauge 1 ½" Precision Glide needle. The STIMEX needles are coated with parylene to prevent electrical conduction throughout the needle, except that the tip that is uncoated. 18 gauge needles were used since the microspheres could not be injected through the 22 gauge STIMEX needles. After the rat was anesthetized, the 18 gauge needle, with inserted 22 gauge STIMEX needle, was placed in the region near the sciatic nerve. (The STIMEX needle had a tape "stop" positioned such that the 22 and 18 gauge needle tips were parallel). One electrode was clamped to the forepaw, and another clamped to the exposed metal region of the STIMEX needle, near the hub. Electrical impulses delivered to the sciatic nerve caused hindlimb flexion, confirming correct needle placement. Upon correct needle placement, the 22 gauge STIMEX needle was removed from the 18 gauge needle, and a 1 cc syringe attached to the 18 gauge needle. The syringe was used for injection of the microspheres and colchicine around the sciatic nerve. Thereafter, paw withdrawal latencies were assessed. A 12 sec time limit was followed in order to prevent damage to the paw. Antiocecption was quantified as the Hot-Plate latency (sec). The group mean Hot-Plate latency ±S.E.M. was calculated for each injected dose and time-point. Significant differences were assessed using repeated measures ANOVA followed by post hoc analyses.

II. Materials and Methods

1. Sciatic Nerve Injection a. Drugs: Microspheres were from Medisorb Technologies International L.P. (Cincinnati, Ohio). The bupivacaine free-base content of the microspheres was: 0.709 g bupivacaine/1,000 g microspheres. Colchicine was added to the aqueous sodium carboxymethylcellulose ("NaCMC") to achieve a final concentration of 0.01% w/w with the bupivacaine free-base content in the microspheres. The microspheres were suspended in diluent (e.g., buffered saline with carboxymethylcellulose) five minutes before injection.

b. Bupivacaine Free-Base ("FB")

A. Bupivacaine FB Dose: 150 mg/kg
B. Injection volume/kg: 0.6 ml/0.275 kg=2.18 ml/kg
C. Concentration of bupivacaine contained in microspheres in diluent: (150 mg/kg)×(kg/2.18 ml)=68.8 mg bupivacaine FB/ml or 0.068 g/ml
D. Concentration of microspheres contained in diluent: (0.068 g bupivacaine FB/ml)×(1 g microspheres/0.709 g bupivacaine FB)=0.097 g microspheres/ml or 97 mg micro21spheres/ml

| | Summary | |
|---|---|---|
| Dose | Concentration Bupivacaine FB | Concentration of microspheres |
| 150 | 68 mg/ml | 97 mg/ml |

III. Colchicine

A. Percent Calculations:
  1. Percent=(gm solute A/100 gm solute B)×100
  2. 0.1%=(0.1 gm colchicine/100 gm Bupivacaine FB)×100

This is also equal to: FB 0.001 gm colchicine/gm Bupivacaine

This is also equal to: FB 0.001 mg colchicine/mg Bupivacaine

B. Colchicine prepared at 0.1% w/w

1. The colchicine concentration that reflects 0.1% w/w with bupivacaine FB is: (0.001 mg colchicine/mg bupivacaine FB)×(68.8 mg bupivacaine FB/ml)=0.0688 mg colchicine/ml 2. Preparation of colchicine
  a. Stock solution was made up at 1 mg/ml in diluent (e.g., buffered saline with carboxymethylcellulose as above)
  b. Dilutions were made to a final concentration of 0.0688 mg/ml

M1×V1=M2×V2

1 mg/ml×V1=6 ml×0.0688 mg/ml

V1=
   0.413 ml stock
   5.587 ml diluent
   6.000 ml final

The dose of colchicine

1. The dose that reflects 0.1% w/w with bupivacaine FB
2. Concentration (mg/ml)×injection volume (ml/kg)=dose (mg/ml) (0.0688 mg colchicine/ml)×(2.18 ml/kg)= 0.150 mg colchicine/kg Table I Local Anesthesia Resulting From (150 mg/kg) Injection Around the Sciatic Nerve of Rats Microspheres were injected around the sciatic nerve of rats after obtaining baseline values of latency (seconds) in the hot-plate test (56° C., 12 second cut-off). Animals were tested at the indicated times.

BMs are bupivacaine microspheres as discussed above.

| Time (hrs) | BMs and 150 mg/kg Colchicine | BMs and 0.01% Colchicine in Solution | BMs and 1% Colchicine in Solution | BMs and 10% Colchicine in Solution | BMs and 10% Colchicine no Microspheres |
|---|---|---|---|---|---|
| Baseline | 1.6 | 3.1 | 3.5 | 3.0 | 2.3 |
| 0.25 | 8.9* | — | 12* | 10.3* | 2.9 |
| 0.5 | 8.8* | — | 10.3* | 11.7* | 2.8 |
| 1 | 9.8* | 11.1* | 10.3* | 12* | 2.3 |
| 3 | 11.2* | 11.7* | 12* | 11.9* | 1.6 |
| 6 | 9.6* | 12.0* | 12* | 11.7* | 2.9 |
| 12 | 7.4* | 8.6* | 9.5* | 12* | 2.5 |
| 24 | 2.7 | 4.0 | 8.7* | 8.6* | 1.8 |

-continued

| Time (hrs) | BMs and 150 mg/kg Colchicine | BMs and 0.01% Colchicine in Solution | BMs and 1% Colchicine in Solution | BMs and 10% Colchicine in Solution | BMs and 10% Colchicine no Microspheres |
|---|---|---|---|---|---|
| 30 | 2.6 | 3.9 | 8.1* | 8.3* | 1.7 |
| 36 | | | 9.8* | 8.9* | |
| 40 | | | 9.8* | | |
| 48 | | | N/A | | |
| 72 | | | 10.3* | see note 1 | see note 2 |
| 84 | | | 8.9* | | |
| 96 | | | 5.4 | | |
| 102 | | | 4.8 | | |
| 108 | | | 5.7 | | |

*Repeated measures ANOVA and Dunnette's t-test for post hoc analyses.

Table II
Local Anesthesia Resulting From SR128-3861 (150 mg/kg) Injection Around the Sciatic Nerve of Rats The experiment reported in Table I was repeated. Microspheres were injected around the sciatic nerve of rats after obtaining baseline values of latency (seconds) in the hot-plate test (56° C., 12 second cut-off). Animals were tested at the indicated times.

| Time (hrs) | BMs (150 mg/kg) | 0.1% Colchicine added to BMS 150 mg/kg | 0.1% Colchicine added to placebo microspheres not 4 |
|---|---|---|---|
| Baseline | 1.6 | 3.0 | 2.7 |
| 0.25 | 8.9* | — | — |
| 0.5 | 8.8* | — | — |
| 1 | 9.8* | 12.0* | 3.0 |
| 3 | 11.2* | 12.0* | 2.9 |
| 6 | 9.6* | 12.0v | 3.3 |
| 12 | 7.4* | 9.9* | 2.9 |
| 24 | 2.7 | 9.8* | 2.9 |
| 30 | 2.6 | 7.4 | 2.8 |
| 36 | | 9.6* | 2.7 |
| 48 | | 11.3* | 2.0 |
| 54 | | 11.8* | 2.1 |
| 60 | | 12.0* | 2.5 |
| 72 | | 10.1* | 2.1 |
| 78 | | 11.1* | 2.8 |
| 84 | | 10.9* | 1.9 |
| 96 | | 9.5* | 2.3 |
| 102 | | 10.5* | 2.5 |
| 108 | | 10.1* | 3.4 |
| 120 | | 12.0* | 3.0 |
| 132 | | 9.7* | 2.6 |
| 144 | | 10.0* | 2.0 |
| 150 | | 10.1* | 3.6 |
| 156 | | 12.0* | 2.5 |
| 168 | | 12.0* | 2.3 |
| 174 | | 6.3* | 2.3 |
| 180 | | 7.1* | 2.4 |
| | | note 3 | note 3 |

*Repeated measures ANOVA and Dunnette's t-test for post hoc analyses.
Note 3: No apparent toxicity.
Note 4: 97 mg.ml of SR128-398 equivalence to 97 mg/ml SR128-3861.

Results

The data tabulated in Table I indicates that the effects of a local anesthetic in controlled release form are prolonged by co-administered colchicine. Table I also shows that as much as 10% colchicine alone has no significant effect on hot-plate foot withdrawal latency and that 1% colchicine in solution combined with bupivacaine in microspheres prolongs the duration of latency out to about 100 hours.

The data tabulated in Table II indicates that 0.1% colchicine in solution, combined with bupivacaine in microspheres prolongs the duration of latency out to about 180 hours, compared to about the 12 hour duration of hot-plate withdrawal latency provided by bupivacaine containing microspheres, without colchicine. Colchicine 0.1% alone injected with placebo microspheres has no effect on latency relative to baseline latency.

The examples provided above are not meant to be exclusive. Many other variations of the present invention would be obvious to those skilled in the art, and are contemplated to be within the scope of the appended claims. Numerous references are cited herein, the disclosures of which are incorporated herein in their entireties.

What is claimed is:

1. A formulation for inducing sustained regional local anesthesia in a patient comprising a substrate comprising a local anesthetic and an effective amount of a biocompatible, biodegradable controlled release material prolonging the release of said local anesthetic from said substrate to obtain a reversible nerve blockade when implanted or injected in a patient, and an amount of colchicine effective to prolong the duration of said local anesthesia for a time period longer than that obtainable from the substrate without said colchicine.

2. The formulation of claim 1, wherein at least a portion of said colchicine is incorporated in said substrate.

3. The formulation of claim 1, wherein at least a portion of said colchicine is in immediate release form.

4. The formulation of claim 1, wherein at least a portion of said colchicine is in controlled release form.

5. The formulation of claim 1, wherein said substrate comprises micro spheres.

6. The formulation of claim 5, wherein said microspheres are suspended in a pharmaceutically acceptable medium for injection.

7. The formulation of claim 1, wherein said colchicine is separately suspended or dissolved in said medium for injection.

8. The formulation of claim 1, wherein the biocompatible material is a polymer selected from the group consisting of polyanhydrides, copolymers of acid and glycolic acid, poly (lactic) acid, poly(glycolic) acid, polyesters, polyorthoesters, proteins, and polysaccharides capable of degrading at least fifty percent in less than two years following implantation into the patient.

9. The formulation of claim 1 wherein the controlled release formulation is in a form selected from the group consisting of slabs, beads, pellets, microparticles, microspheres, microcapsules, spheroids and pastes.

10. The formulation of claim 1, wherein the local anesthetic is incorporated into said controlled release material at a percent loading of 0.1% to 90% by weight.

11. The formulation of claim 10 wherein the local anesthetic is selected from the group consisting of bupivacaine, dibucaine, etidocaine, tetracaine, lidocaine, xylocaine, mixtures thereof, and salts thereof.

12. The formulation of claim 1 wherein said colchicine is effective to increase the duration of local anesthesia in a range from 2 to 15 times the duration of local anesthesia induced by controlled release local anesthetic without the colchicine.

13. The formulation of claim 12 wherein said colchicine is incorporated into said substrate at a percent loading of 0.01 to 30% by weight.

14. The formulation of claim 12 wherein said colchicine is present in a weight percentage relative to the local anesthetic ranging from about 0.013% to about 10%.

15. The formulation of claim 12 wherein said colchicine is present in a weight percentage of the pharmaceutical formulation ranging from about 0.05% to about 5%.

16. The formulation of claim 12 providing prolonged reversible nerve blockade for at least about 180 hours.

17. The formulation of claim 1 wherein said formulation provides prolonged reversible nerve blockade for at least about 200 hours.

18. A formulation for inducing sustained regional local anesthesia in a patient comprising a substrate comprising a local anesthetic and an effective amount of a biocompatible, biodegradable, controlled release material for prolonging the release of said local anesthetic from said substrate to obtain a reversible nerve blockade when implanted or injected in a patient, and an amount of colchicine effective to prolong the duration of said local anesthesia, said formulation providing an in vitro release of said local anesthetic of from about 10 to about 60 percent after 24 hours, from about 20 to about 80 percent release after 48 hours and from about 40 to about 100 percent release after 72 hours, said formulation providing a reversible nerve blockade at the site when administered in vivo of at least about 24 hours.

19. The formulation of claim 18, wherein the formulation provides from about 40 to about 50 percent release after 24 hours and from about 45 to about 55 percent release after 72 hours and from about 80 to about 100 percent release after about 280 hours and which provides at least about 40 hours of local anesthetic activity when administered in vivo.

20. The formulation of claim 18 that provides local anesthetic activity ranging from about 24 to about 200 hours.

21. A controlled release formulation for inducing sustained regional local anesthesia at a site in a patient comprising a local anesthetic incorporated in a controlled release formulation consisting essentially of a biocompatible material, said material degrading at least fifty percent in less than six months following implantation into a patient, wherein the local anesthetic is present in a concentration effective to achieve local anesthesia in the patient, and an amount of colchicine effective to prolong the duration of the local anesthesia.

22. A method for inducing sustained regional local anesthesia at a site in a patient, comprising:

preparing a local anesthetic in a biocompatible, biodegradable controlled release form such that the percent release of said local anesthetic in vivo is from about 10 to about 60 percent release after 24 hours, from about 20 to about 80 percent after 48 hours, and from about 40 to about 100 percent release after 72 hours, administering an effective amount of said local anesthetic in controlled release form to achieve a reversible nerve blockade at the site, and administering an amount of colchicine at the site, that is effective to achieve a reversible nerve blockade at the site for at least about 24 hours.

23. The method of claim 22, further comprising preparing at least a portion of said colchicine in controlled release form.

24. The method of claim 22, further comprising preparing said controlled release form as a plurality of microspheres, suspending said microspheres in a pharmaceutically acceptable medium for injection, and injecting said microspheres at the site.

25. The method of claim 24, further comprising incorporating at least a portion of said colchicine into said medium for injection.

26. The method of claim 22, further comprising injecting or implanting said formulation in proximity to a nerve to be anesthetized.

27. The method of claim 22, further comprising administering at least a portion of said colchicine after administration of said local anesthetic.

28. The method of claim 24 wherein the local anesthetic is incorporated into said plurality of controlled release microspheres comprising a biodegradable polymer at a percent loading of 0.1% to 90%.

29. The method of claim 24, wherein the colchicine that is incorporated into said microspheres at a percent loading of 0.01 to 30% by weight.

30. The method of claim 22 wherein the local anesthetic is bupivacaine.

31. The method of claim 30 wherein the bupivacaine is administered in a dose ranging from 5 through 450 mg/kg of a patient.

32. The method of claim 22 wherein the prolonged duration of local anesthesia ranges from 2 to 15 times the duration of local anesthesia induced by controlled release local anesthetic without said colchicine.

33. The method of claim 22 wherein said colchicine is present in a weight percentage relative to the local anesthetic ranging from about 0.01% to about 10%.

* * * * *